United States Patent
Cui et al.

(10) Patent No.: US 11,332,417 B2
(45) Date of Patent: May 17, 2022

(54) SYSTEM AND METHOD FOR PREPARING AROMATICS BY USING SYNGAS

(71) Applicants: Huadian Coal Industry Group Co., Ltd., Beijing (CN); Tsinghua University, Beijing (CN)

(72) Inventors: Yu Cui, Beijing (CN); Xiaofan Huang, Beijing (CN); Xiaoping Tang, Beijing (CN); Tong Wang, Beijing (CN); Weizhong Qian, Beijing (CN); Fei Wei, Beijing (CN); Changping Gao, Beijing (CN); Xiulin Wang, Beijing (CN); Zuoru Yin, Beijing (CN)

(73) Assignees: HUADIAN COAL INDUSTRY GROUP CO., LTD., Beijing (CN); TSINGHUA UNIVERSITY, Beijing (CN)

( * ) Notice: Subject to any disclaimer, the term of this patent is extended or adjusted under 35 U.S.C. 154(b) by 15 days.

(21) Appl. No.: 16/626,715

(22) PCT Filed: Jun. 30, 2017

(86) PCT No.: PCT/CN2017/091068
§ 371 (c)(1),
(2) Date: Dec. 26, 2019

(87) PCT Pub. No.: WO2019/000381
PCT Pub. Date: Jan. 3, 2019

(65) Prior Publication Data
US 2020/0157021 A1 May 21, 2020

(51) Int. Cl.
*C07C 1/04* (2006.01)
*C07C 15/04* (2006.01)
*C07C 15/06* (2006.01)
*C07C 15/08* (2006.01)

(52) U.S. Cl.
CPC ............ *C07C 1/0405* (2013.01); *C07C 1/044* (2013.01); *C07C 15/04* (2013.01); *C07C 15/06* (2013.01); *C07C 15/08* (2013.01); *C07C 2529/40* (2013.01)

(58) Field of Classification Search
CPC ..... C07C 1/0405; C07C 1/044; C07C 1/0485; C07C 15/04; C07C 15/06; C07C 15/08;
(Continued)

(56) References Cited

U.S. PATENT DOCUMENTS 4,180,516 A * 12/1979 Chang ...................... B01J 23/26
502/71
2010/0144907 A1 6/2010 Kibby et al.
(Continued)

FOREIGN PATENT DOCUMENTS

CN 1880288 12/2006
CN 101270297 9/2008
(Continued)

OTHER PUBLICATIONS

International Search Report, issued in the corresponding PCT application No. PCT/CN2017/091068, dated Apr. 4, 2018 (8 pages).

*Primary Examiner* — Youngsul Jeong
*Assistant Examiner* — Jason Y Chong
(74) *Attorney, Agent, or Firm* — Hamre, Schumann, Mueller & Larson, P.C.

(57) ABSTRACT

The present invention relates to a system and process for preparing aromatics from syngases, which has advantages of shortened flow process and reduced investment. The process comprises reforming the liquefied gas, separated dry gas with a water steam to produce carbon monoxide and hydrogen, which return, as raw materials, to the aromatization system, so that the problem of by-product utilization is solved, and the syngas unit consumption per ton of aromatic (Continued)

products is reduced. The problem of utilization of a dry gas as a by-product is also solved in the present invention from the perspective of recycling economy, which reduces the water consumption in the process, and conforms to the concept of green chemistry.

6 Claims, 2 Drawing Sheets

(58) Field of Classification Search
CPC ............ C07C 2529/40; C07C 2529/44; C07C 2529/46; C07C 7/005; C07C 7/09; C01B 3/24; C01B 3/30; C10G 31/06; C10G 33/00; C10G 2/334; C10G 2400/30
See application file for complete search history.

(56) References Cited

U.S. PATENT DOCUMENTS

2016/0024393 A1\* 1/2016 Beech, Jr. ............. B01J 29/064
585/321
2019/0031575 A1\* 1/2019 Pan .................... B01J 29/48

FOREIGN PATENT DOCUMENTS

| | | | |
|---|---|---|---|
| CN | 104326859 | | 2/2015 |
| CN | 104326859 A | \* | 2/2015 |
| CN | 104557415 A | \* | 4/2015 |
| CN | 106268924 | | 1/2017 |
| CN | 106588526 | | 4/2017 |
| WO | 2014/001354 | | 1/2014 |

\* cited by examiner

SYSTEM AND METHOD FOR PREPARING AROMATICS BY USING SYNGAS

This application is a National Stage of International Application No. PCT/CN2017/091068, filed Jun. 30, 2017, which is hereby incorporated by reference in their entireties.

TECHNICAL FIELD

The present invention relates to a system and process for preparing aromatics from syngases, which pertains to the technical field of petrochemical technology.

BACKGROUND

"BMX (Benzene, Methylbenzene, Xylene)" and "EPB (Ethylene, Propylene, Butadiene)" are basic chemical raw materials in the petrochemical industry. Among them, "BMX", as the main aromatic material, is mainly derived from petroleum refining and coal retorting traditionally. Currently, 70% or more of aromatics are obtained by petroleum route which particularly comprises using naphtha as raw material, and subjecting to aromatics reforming and aromatics combination process to obtain aromatic raw materials mainly composed of benzene and p-xylene, which is basic chemical raw materials for subsequent process for preparing various synthetic fibers and new chemical materials. However, as the increasing shortage of petroleum resources, the aromatics is kept in short supply with a high price, which greatly affects the supply of raw materials for the downstream industries of chemical fibers and new materials.

In recent years, a process route for preparing aromatics from alcohol ethers using methanol and dimethyl ether as the main raw materials has been developed in the art, which process generally comprises using coal as the raw material, subjecting to gasification, conversion, methanol synthesis and purification, and then preparing aromatics from methanol. The process can reduce the dependence of aromatic raw materials on petroleum to a certain extent, however, it has disadvantages such as long production route, enormous investment, and high energy consumption. Meanwhile, the process of producing methanol from coal requires large consumption of water, while in turn, water is produced in the process of obtaining aromatics from methanol, which results in waste of water resource.

Chinese patent application CN1880288A discloses a technique of methanol/dimethyl ether aromatization, which uses a modified ZSM-5 catalyst, and separates the products into gas-phase and oil-phase products after cooling, wherein the oil-phase product is subjected to extraction to obtain aromatics and non-aromatics. As compared with the current coal-to-methanol process route, it is shown that this process has disadvantages such as a long path and enormous investment.

SUMMARY OF THE INVENTION

In view of the above technical problems, the present invention is to provide a system and process for preparing aromatics from syngases, which process can synthesize aromatics using syngases in one step, thereby overcomes the disadvantages of the methanol-to-aromatics process, such as long process path, enormous investment, and high energy consumption.

In order to achieve the above object, firstly, it is provided a system for preparing aromatics from syngases, comprising: a syngas purification unit, a syngas conversion unit, a syngas-to-aromatics unit, a gas-liquid separation unit, a liquefied-gas separation unit, a dry-gas separation unit, a dry-gas conversion unit and an oil-water separation unit,
wherein the syngas purification unit, the syngas conversion unit, the syngas-to-aromatics unit, and the gas-liquid separation unit are sequentially connected;
the gas-liquid separation unit is connected to the liquefied-gas separation unit and the oil-water separation unit, respectively;
the liquefied-gas separation unit is connected to the dry-gas separation unit;
the dry-gas separation unit is connected to the dry-gas conversion unit and the syngas-to-aromatics unit, respectively; and
the dry-gas conversion unit is connected to the syngas-to-aromatics unit.

In the system,
the syngas purification unit is configured to purify the syngas as a raw material;
the syngas conversion unit is configured to adjust the ratio of hydrogen to carbon monoxide in the syngas;
the syngas-to-aromatics unit is configured to contact gas with a catalyst to produce aromatics;
the gas-liquid separation unit is configured to separate the aromatic products into a gas phase and a liquid phase;
the liquefied-gas separation unit is configured to separate the gas phase separated by the gas-liquid separation unit into a liquefied gas and a dry gas, wherein the liquefied gas is output as a product, and the dry gas is introduced into the dry-gas separation unit;
the dry-gas separation unit is configured to separate the dry gas separated by the liquefied-gas separation unit into hydrogen, carbon monoxide and methane, ethane, ethylene and carbon dioxide, wherein methane and ethane may be introduced into the dry-gas conversion unit to be converted into syngas (i.e., hydrogen and carbon monoxide); alternatively, a part of methane, a part of ethane and the entire ethylene may be removed for other purposes, while all of the remaining methane and ethane may be introduced into the dry-gas conversion unit to be converted into syngas;
the dry-gas conversion unit is configured to convert gas from the dry-gas separation unit into syngas;
the oil-water separation unit is configured to separate the liquid phase separated by gas-liquid separation unit into an oil phase (e.g., aromatics) and an aqueous phase, which are then introduced into the corresponding post-system for processing, respectively.

In the above system, preferably, the liquefied-gas separation unit is connected to the syngas-to-aromatics unit, to supply the liquefied gas and ethylene to the syngas-to-aromatics unit, so that the liquefied gas and ethylene produced by the syngas-to-aromatics unit return to the separated syngas-to-aromatics unit to further increase the yield of aromatics.

It is also provided a process for preparing aromatics from syngases by using the above system, comprising the steps of:
a) supplying syngases as raw materials into a syngas purification unit for purification;
b) introducing the purified syngases into a syngas conversion unit for conversion;
c) introducing the converted syngases, carbon monoxide and hydrogen from a dry-gas conversion unit, carbon monoxide and hydrogen from the dry-gas separation unit into a syngas-to-aromatics unit to produce aromatics;

d) cooling the reaction product obtained in step c), then introducing it into a gas-liquid three-phase separation unit to separate into a gas phase and a liquid phase, wherein the gas phase is introduced into the liquefied-gas separation unit to separate into a liquefied gas and a dry gas, and the liquid phase is introduced into the oil-water separation unit to separate into an oil phase and a aqueous phase;

e) introducing the dry gas obtained in step d) into a dry-gas separation unit to separate into hydrogen, carbon monoxide and methane, ethane, ethylene, carbon dioxide; and f) introducing methane and ethane obtained in step e) into a dry-gas conversion unit to convert into syngases, that is, hydrogen and carbon monoxide.

In the above process, preferably, in step c), the catalyst used for preparing the aromatics in the syngas-to-aromatics unit is a composite catalyst which comprises a support and a first metal component and a second metal component. Among these, the support as used comprises one or more selected from a ZSM-5 molecular sieve, a ZSM-11 molecular sieve and a ZSM-22 molecular sieve; the first metal component is one or more selected from zinc, silver, gallium, lanthanum and cerium, and is comprised in an amount of 0.1% to 10% of the total mass of the catalyst, based on the metal; the second metal component is one or more selected form iron, cobalt, chromium, manganese, and copper, and is comprised in an amount of 10% to 60% of the total mass of the catalyst, based on the metal. The molecular sieve as the support is comprised in an amount of 30% to 90% of the total mass of the catalyst, wherein the total mass of the carrier, the first metal component and the second metal component is 100%.

In the above process, preferably, in step d), the liquefied gas separated by the liquefied-gas separation unit is introduced into the syngas-to-aromatics unit to produce aromatics.

In the above process, preferably, in step e), a part of hydrogen and carbon monoxide separated by the dry-gas separation unit is introduced into an aromatics-processing unit.

In the above process, preferably, in step f), a part of methane, a part of ethane and the entire ethylene is removed, and all of the remaining methane and ethane are introduced into the dry-gas conversion unit to convert into syngases, that is, hydrogen and carbon monoxide.

In the above process, preferably, in step c), the reaction temperature in the syngas-to-aromatics unit is from 300° C. to 550° C., preferably from 380° C. to 520° C.

In the above method, preferably, in step c), the volume space velocity in the syngas-to-aromatics unit is from 100 $h^{-1}$ to 100,000 $h^{-1}$ preferably 1,000 $h^{-1}$ to 10,000 $h^{-1}$.

In the above method, preferably, in step c), the reaction pressure in the syngas-to-aromatics unit is from 1.0 MPa to 10.0 MPa.

In the above method, preferably, in step c), the molar ratio of carbon monoxide to hydrogen in the converted syngases at the outlet of the syngas conversion unit is 1.0-3.5:1, preferably 1.5-3.0:1.

In the above method, preferably, in step f), the syngas is prepared by conversion in the dry-gas conversion unit under a conversion pressure of 1.5 MPa to 4.0 MPa and a conversion temperature of 800° C. to 1000° C.

In the above method, the separation of a gas phase and a liquid phase in the gas-liquid three-phase separation unit may be carried out by a conventional cooling and separation procedure; the separation of the gas phase in the liquefied-gas separation unit into a liquefied gas and a dry gas may be carried out by a conventional oil absorption separation procedure; and the separation of the liquid phase in the oil-water separation unit into an oil phase and a aqueous phase may be carried out by a conventional oil-water separation procedure. In step e), the separation of the dry gas in the dry-gas separation unit is carried out by a combined separation of cool-oil absorption and adsorbent adsorption.

The aromatization of coal via alcohol ether has disadvantages of long production path, enormous investment and high energy consumption, while the coal-to-methanol process requires high water consumption and wastes a large amount of carbon monoxide for water-gas conversion to provide hydrogen for methanol synthesis, and the methanol-to-aromatics process will regenerate water, which results in massive waste of water resources. In view of this, the system and process for preparing aromatics from syngases as provided in the present invention is to overcome the disadvantages of the aromatization of coal via alcohol ether such as long production path, enormous investment and high energy consumption, by using syngas to produce aromatics in one step, resulting in the investment reduced by more than 15%, and the energy consumption reduced by more than 20%.

The invention further provides a method for using a dry gas as a by-product in the aromatization of syngases, which comprises reforming the separated dry gas with a water steam to produce carbon monoxide and hydrogen, which return, as syngases, to the aromatization system, so that the problem of by-product utilization is solved, and the syngas unit consumption per ton of aromatic products is reduced.

In another aspect, since water is generated in the product of syngas aromatization in a small amount, the requirement on hydrogen-carbon ratio of the reaction feed is lowered, the load of the syngas conversion is reduced greatly, and the water consumption is decreased, as compared to those in the prior coal-to-aromatics system.

Meanwhile, the present invention further provides a method for increasing the productivity of aromatics by returning the liquefied gas, as a by-product in the process for preparing aromatics from syngases, to the syngas-to-aromatics reaction system, so that the problem of liquefied-gas utilization is solved and the yield of aromatics is increased.

The present invention solves the problem of utilization of a dry gas as a by-product, and reduces the water consumption in the process from the perspective of recycling economy, and thus conforms to the concept of green chemistry.

SYMBOLS FOR MAIN COMPONENTS 1. syngas purification unit;
2. syngas conversion unit;
3. syngas-to-aromatics unit;
4. gas-liquid separation unit;
5. liquefied-gas separation unit;

6. dry-gas separation unit;
7. dry-gas conversion unit;
8. oil-water separation unit.

DETAILED DESCRIPTION OF EMBODIMENTS

The present invention provides a system and process for preparing aromatics from syngases, which is further illustrated by reference to the accompanying drawings in the following.

Example 1

Figure 1:
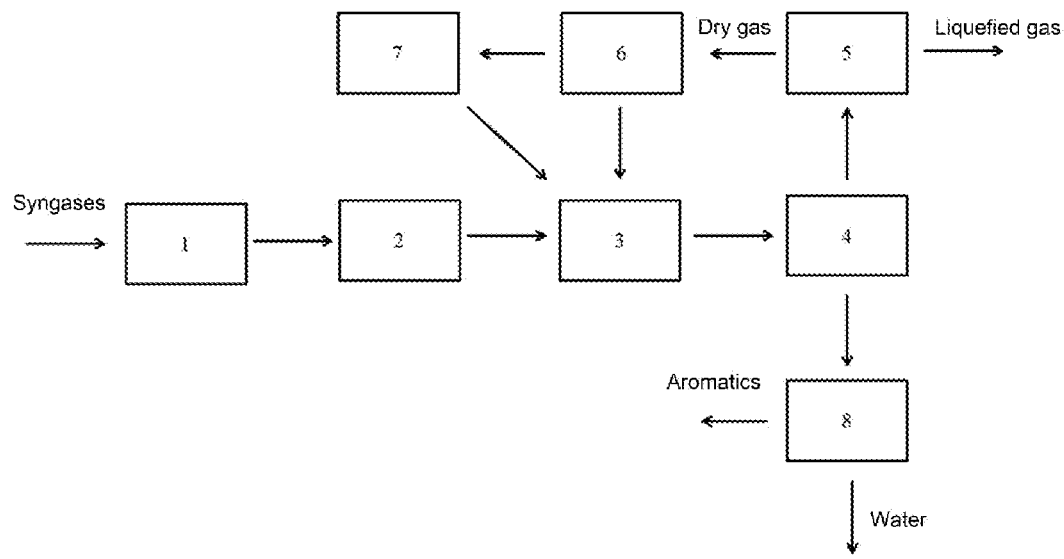
FIG. 1 is a process flow diagram of the system and process for preparing aromatics from syngases as provided in Example 1.

A system for preparing aromatics from syngases is provided in this Example, the structure of which is shown in FIG. 1. The system comprises: a syngas purification unit 1, a syngas conversion unit 2, a syngas-to-aromatics unit 3, a gas-liquid separation unit 4, a liquefied-gas separation unit 5, a dry-gas separation unit 6, a dry-gas conversion unit 7 and an oil-water separation unit 8,
- wherein the syngas purification unit 1, the syngas conversion unit 2, the syngas-to-aromatics unit 3, and the gas-liquid separation unit 4 are sequentially connected;
- the outlets of the gas-liquid separation unit are connected to the liquefied-gas separation unit 5 and the oil-water separation unit 8, respectively;
- the outlet of the liquefied-gas separation unit 5 is connected to the dry-gas separation unit 6;
- the outlets of the dry-gas separation unit 6 are connected to the dry-gas conversion unit 7 and the syngas-to-aromatics unit 3, respectively; and
- the outlet of the dry-gas conversion unit 7 is connected to the syngas-to-aromatics unit 3.

When using the system as provided in this Example to produce aromatics from syngases, a process comprising the following steps may be performed (according to the process flow diagram as shown in FIG. 1):
- the syngases as raw materials are supplied into the syngas purification unit 1 for purification;
- the purified syngases are introduced into the syngas conversion unit 2 to produce converted gases having a ratio of $H_2:CO=1.5:1$;
- the gas is introduced into the syngas-to-aromatics unit 3 for reaction, wherein the catalyst as used comprises a support of a ZSM-5 molecular sieve, a first metal of zinc and ruthenium, and a second metal of iron, cobalt and manganese, with a ratio by mass of ZSM-5 molecular sieve, metal zinc, metal cerium, metal iron, metal cobalt, and metal manganese (ZSM-5:zinc:cerium:iron:cobalt:manganese) of 55:3:1:1:3:36; the reaction is carried out at a reaction temperature of 475° C., a reaction pressure of 2.5 MPa, and a volume space velocity of 5000 $h^{-1}$; the gas is converted into a gas phase, a aqueous phase, oil-phase components such as non-aromatics, benzene, toluene, $C_8$ aromatics, $C_9$ aromatics, $C_{10}$ aromatics and heavy aromatics under the action of the catalyst, while the composition thereof is as shown in Table 1. The resultant products are introduced into the gas-liquid separation unit 4 to separate into a gas-phase product and a liquid-phase product, wherein the liquid-phase product is introduced into the oil-water separation unit 8 to separate into an oil phase and an aqueous phase, and the oil phase and an aqueous phase are introduced into corresponding downstream systems for treatment, respectively.

The gas phase product separated by the gas-liquid separation unit 4 is introduced into the liquefied-gas separation unit 5 to separate into a liquefied gas and a part of ethylene and dry gas, wherein the liquefied gas and ethylene are used as products, while the dry gas is introduced into the dry-gas separation unit 6 to separate into hydrogen, carbon monoxide and methane, ethane, ethylene and carbon dioxide; among them, hydrogen and carbon monoxide are returned to the syngas-to-aromatics unit 3 for reaction, while methane and ethane are introduced into the dry-gas conversion unit 7 to convert into syngases, i.e. hydrogen and carbon monoxide, under a conversion temperature of 900° C. and a conversion pressure of 3.0 MPa, which products are then returned to the syngas-to-aromatics unit 3.

TABLE 1

The reaction products in the preparation of aromatics from syngases

| Products | Selectivity of hydrocarbonyls % |
|---|---|
| Dry gas | 11 |
| Liquefied gas | 22 |
| Oil-phase non-aromatics | 9 |
| Aromatics | 55 |
| CO conversion rate (excluding conversion to $CO_2$) | 25 |

Example 2

A process for preparing aromatics from syngases is provided in this Example, which is carried out by using the system in Example 1, and comprises the following steps:
- the syngases as raw materials are supplied into the syngas purification unit 1 for purification;
- the purified syngases are introduced into the syngas conversion unit 2 to produce converted gases having a ratio of $H_2:CO=2.0:1$;
- the gas is introduced into the syngas-to-aromatics unit 3 for reaction, wherein the catalyst as used comprises a support of a ZSM-11 molecular sieve, a first metal of zinc and lanthanum, and a second metal of iron, cobalt and copper, with a ratio by mass of ZSM-11 molecular sieve, metal zinc, metal lanthanum, metal iron, metal cobalt, and metal copper (ZSM-11:zinc:lanthanum:iron:cobalt:copper) of 55:3:1:1:4:36; the reaction is carried out at a reaction temperature of 300° C., a reaction pressure of 10 MPa, and a volume space velocity of 10000 $h^{-1}$; the gas is converted into a gas phase, a aqueous phase, oil-phase components such as non-aromatics, benzene, toluene, $C_8$ aromatics, $C_9$ aromatics, $C_{10}$ aromatics and heavy aromatics under the action of the catalyst, while the composition thereof is as shown in Table 2. The resultant products are introduced into the gas-liquid separation unit 4 to separate into a gas-phase product and a liquid-phase product, wherein the liquid-phase product is introduced into the oil-water separation unit 8 to separate into an oil phase and an aqueous phase, the oil phase and aqueous phase are introduced into corresponding downstream systems for treatment, respectively.

The gas phase product separated by the gas-liquid separation unit 4 is introduced into the liquefied-gas separation unit 5 to separate into a liquefied gas and a part of ethylene and dry gas, wherein the liquefied gas and ethylene are used as products, while the dry gas is introduced into the dry-gas separation unit 6 to separate into hydrogen, carbon monoxide and methane, ethane, ethylene and carbon dioxide; among them, hydrogen and carbon monoxide are returned to the syngas-to-aromatics unit 3 for reaction, while methane and ethane are introduced into the dry-gas conversion unit 7 to convert into syngases, i.e. hydrogen and carbon monoxide, under a conversion temperature of 1000° C. and a conversion pressure of 2.0 MPa, which products are then returned to the syngas-to-aromatics unit 3.

TABLE 2

The reaction products in the preparation of aromatics from syngases

| Products | Selectivity of hydrocarbonyls % |
|---|---|
| Dry gas | 12 |
| Liquefied gas | 21 |
| Oil-phase non-aromatics | 13 |
| Aromatics | 49 |
| CO conversion rate (excluding conversion to $CO_2$) | 22 |

Example 3

A process for preparing aromatics from syngases is provided in this Example, which is carried out by using the system in Example 1, and comprises the following steps:

the syngases as raw materials are supplied into the syngas purification unit 1 for purification;

the purified syngases are introduced into the syngas conversion unit 2 to produce converted gases having a ratio of $H_2:CO=3.5:1$;

the gas is introduced into the syngas-to-aromatics unit 3 for reaction, wherein the catalyst as used comprises a support of a ZSM-22 molecular sieve, a first metal of zinc and gallium, and a second metal of iron and cobalt, with a ratio by mass of ZSM-22 molecular sieve, metal zinc, metal gallium, metal iron and metal cobalt (ZSM-22:zinc:gallium:iron:cobalt) of 44:3:1:22:30; the reaction is carried out at a reaction temperature of 550° C., a reaction pressure of 1.0 MPa, and a volume space velocity of 100000 $h^{-1}$; the gas is converted into a gas phase, a aqueous phase, oil-phase components such as non-aromatics, benzene, toluene, $C_8$ aromatics, $C_9$ aromatics, $C_{10}$ aromatics and heavy aromatics under the action of the catalyst, while the composition thereof is as shown in Table 3. The resultant products are introduced into the gas-liquid separation unit 4 to separate into a gas-phase product and a liquid-phase product, wherein the liquid-phase product is introduced into the oil-water separation unit 8 to separate into an oil phase and an aqueous phase, the oil phase and aqueous phase are introduced into corresponding downstream systems for treatment, respectively.

The gas phase product separated by the gas-liquid separation unit 4 is introduced into the liquefied-gas separation unit 5 to separate into a liquefied gas and a part of ethylene and dry gas, wherein the liquefied gas and ethylene are used as products, while the dry gas is introduced into the dry-gas separation unit 6 to separate into hydrogen, carbon monoxide and methane, ethane, ethylene and carbon dioxide; among them, hydrogen and carbon monoxide are returned to the syngas-to-aromatics unit 3 for reaction, while methane and ethane are introduced into the dry-gas conversion unit 7 to convert into syngases, i.e. hydrogen and carbon monoxide, under a conversion temperature of 800° C. and a conversion pressure of 2.0 MPa, which products are then returned to the syngas-to-aromatics unit 3.

TABLE 3

The reaction products in the preparation of aromatics from syngases

| Products | Selectivity of hydrocarbonyls % |
|---|---|
| Dry gas | 15 |
| Liquefied gas | 12 |
| Oil-phase non-aromatics | 13 |
| Aromatics | 56 |
| CO conversion rate (excluding conversion to $CO_2$) | 35 |

Example 4

Figure 2:
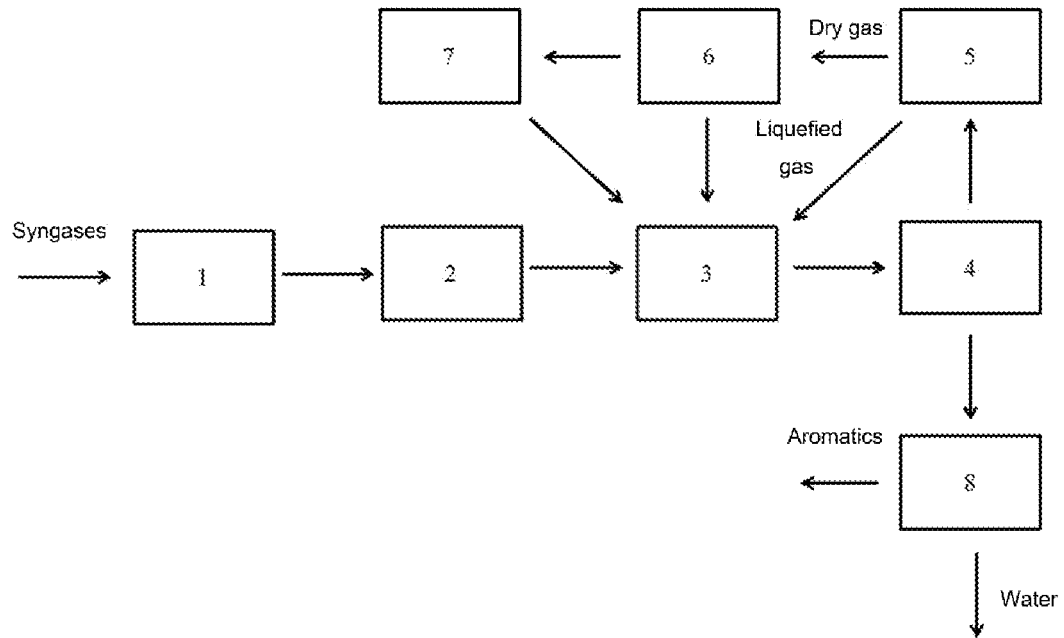
FIG. 2 is a process flow diagram of the system and process for preparing aromatics from syngases as provided in Example 5.

A system for preparing aromatics from syngases is provided in this Example, the structure of which is shown in FIG. 2. The system comprises: a syngas purification unit 1, a syngas conversion unit 2, a syngas-to-aromatics unit 3, a gas-liquid separation unit 4, a liquefied-gas separation unit 5, a dry-gas separation unit 6, a dry-gas conversion unit 7 and an oil-water separation unit 8, wherein the syngas purification unit 1, the syngas conversion unit 2, the syngas-to-aromatics unit 3, and the gas-liquid separation unit 4 are sequentially connected;

the outlets of the gas-liquid separation unit 4 are connected to the liquefied-gas separation unit 5 and the oil-water separation unit 8, respectively;

the outlets of the liquefied-gas separation unit 5 are connected to the dry-gas separation unit 6 and the syngas-to-aromatics unit 3, respectively;

the outlets of the dry-gas separation unit 6 are connected to the dry-gas conversion unit 7 and the syngas-to-aromatics unit 3, respectively; and the outlet of the dry-gas conversion unit 7 is connected to the syngas-to-aromatics unit 3.

When using the system as provided in this Example to produce aromatics from syngases, a process comprising the following steps may be performed (according to the process flow diagram as shown in FIG. 2):

the syngases as raw materials are supplied into the syngas purification unit 1 for purification;

the purified syngases are introduced into the syngas conversion unit 2 to produce converted gases having a ratio of $H_2:CO=2.5:1$;

the gas is introduced into the syngas-to-aromatics unit 3 for reaction, wherein the catalyst as used comprises a support of a ZSM-5 molecular sieve, a first metal of zinc and lanthanum, and a second metal of iron and cobalt, with a ratio by mass of ZSM-5 molecular sieve, metal zinc, metal lanthanum, metal iron and metal cobalt (ZSM-5:zinc:lanthanum:iron:cobalt) of 54:3:1:15:27; the reaction is carried out at a reaction temperature of 450° C., a reaction pressure of 4.0 MPa, and a volume space velocity of 10000 $h^{-1}$; the gas is converted into a gas phase, a aqueous phase, oil-phase components such as non-aromatics, benzene, toluene, $C_8$ aromatics, $C_9$ aromatics, $C_{10}$ aromatics and heavy aromatics under the action of the catalyst, while the composition thereof is as shown in Table 4. The resultant products are introduced into the gas-liquid separation unit 4 to separate into a gas-phase product and a liquid-phase product, wherein the liquid-phase product is introduced into the oil-water separation unit 8 to separate into an oil phase and an aqueous phase, and the oil phase and aqueous phase are introduced into corresponding downstream systems for treatment, respectively.

The gas phase product separated by the gas-liquid separation unit 4 is introduced into the liquefied-gas separation unit 5 to separate into a liquefied gas and a part of ethylene and dry gas, wherein the liquefied gas and ethylene are returned to the syngas-to-aromatics unit 3, while the dry gas is introduced into the dry-gas separation unit 6 to separate into hydrogen, carbon monoxide and methane, ethane, ethylene and carbon dioxide; among them, hydrogen and carbon monoxide are returned to the syngas-to-aromatics unit 3 for reaction, while methane and ethane are introduced into the dry-gas conversion unit 7 to convert into syngases, i.e. hydrogen and carbon monoxide, under a conversion temperature of 800° C. and a conversion pressure of 2.0 MPa, which products are then returned to the syngas-to-aromatics unit 3.

TABLE 4

The reaction products in the preparation of aromatics from syngases, excluding supplied liquefied gas

| Products | Selectivity of hydrocarbonyls % |
| --- | --- |
| Dry gas | 8 |
| Liquefied gas | 13 |
| Oil-phase non-aromatics | 7 |
| Aromatics | 67 |
| CO conversion rate (excluding conversion to $CO_2$) | 26 |

Example 5

A system for preparing aromatics from syngases is provided in this Example, the structure of which is shown in FIG. 2. The system comprises, a syngas purification unit 1, a syngas conversion unit 2, a syngas-to-aromatics unit 3, a gas-liquid separation unit 4, a liquefied-gas separation unit 5, a dry-gas separation unit 6, a dry-gas conversion unit 7 and an oil-water separation unit 8, wherein the syngas purification unit 1, the syngas conversion unit 2, the syngas-to-aromatics unit 3, and the gas-liquid separation unit 4 are sequentially connected;

the outlets of the gas-liquid separation unit 4 are connected to the liquefied-gas separation unit 5 and the oil-water separation unit 8, respectively;

the outlets of the liquefied-gas separation unit 5 are connected to the dry-gas separation unit 6 and the syngas-to-aromatics unit 3, respectively;

the outlets of the dry-gas separation unit 6 are connected to the dry-gas conversion unit 7 and the syngas-to-aromatics unit 3, respectively; and the outlet of the dry-gas conversion unit 7 is connected to the syngas-to-aromatics unit 3.

When using the system as provided in this Example to produce aromatics from syngases, a process comprising the following steps may be performed (according to the process flow diagram as shown in FIG. 2):

the syngases as raw materials are supplied into the syngas purification unit 1 for purification;

the purified syngases are introduced into the syngas conversion unit 2 to produce converted gases having a ratio of $H_2:CO=2:1$;

the gas is introduced into the syngas-to-aromatics unit 3 for reaction, wherein the catalyst as used comprises a support of a ZSM-11 molecular sieve, a first metal of zinc and silver, and a second metal of iron and copper, with a ratio by mass of ZSM-11 molecular sieve, metal zinc, metal silver, metal iron and metal copper (ZSM-11:zinc:silver:iron:copper) of 65:3:2:12:18; the reaction is carried out at a reaction temperature of 475° C., a reaction pressure of 2.5 MPa, and a volume space velocity of 5000 $h^{-1}$; the gas is converted into a gas phase, a aqueous phase, oil-phase components such as non-aromatics, benzene, toluene, $C_8$ aromatics, $C_9$ aromatics, $C_{10}$ aromatics and heavy aromatics under the action of the catalyst, while the composition thereof is as shown in Table 5. The resultant products are introduced into the gas-liquid separation unit 4 to separate into a gas-phase product and a liquid-phase product, wherein the liquid-phase product is introduced into the oil-water separation unit 8 to separate into an oil phase and an aqueous phase, and the oil phase and aqueous phase are introduced into corresponding downstream systems for treatment, respectively.

The gas phase product separated by the gas-liquid separation unit 4 is introduced into the liquefied-gas separation unit 5 to separate into a liquefied gas and a part of ethylene and dry gas, wherein the liquefied gas and ethylene are returned to the syngas-to-aromatics unit 3, while the dry gas is introduced into the dry-gas separation unit 6 to separate into hydrogen, carbon monoxide and methane, ethane, ethylene and carbon dioxide; among them, hydrogen and carbon monoxide are returned to the syngas-to-aromatics unit 3 for reaction, while methane and ethane are introduced into the dry-gas conversion unit 7 to convert into syngases, i.e. hydrogen and carbon monoxide, under a conversion temperature of 900° C. and a conversion pressure of 3.0 MPa, which products are then returned to the syngas-to-aromatics unit 3.

TABLE 5

The reaction products in the preparation of aromatics from syngases, excluding supplied liquefied gas

| Products | Selectivity of hydrocarbonyls % |
| --- | --- |
| Dry gas | 10 |
| Liquefied gas | 11 |
| Oil-phase non-aromatics | 4 |
| Aromatics | 73 |
| CO conversion rate (excluding conversion to $CO_2$) | 40 |

Example 6

Figure 3:
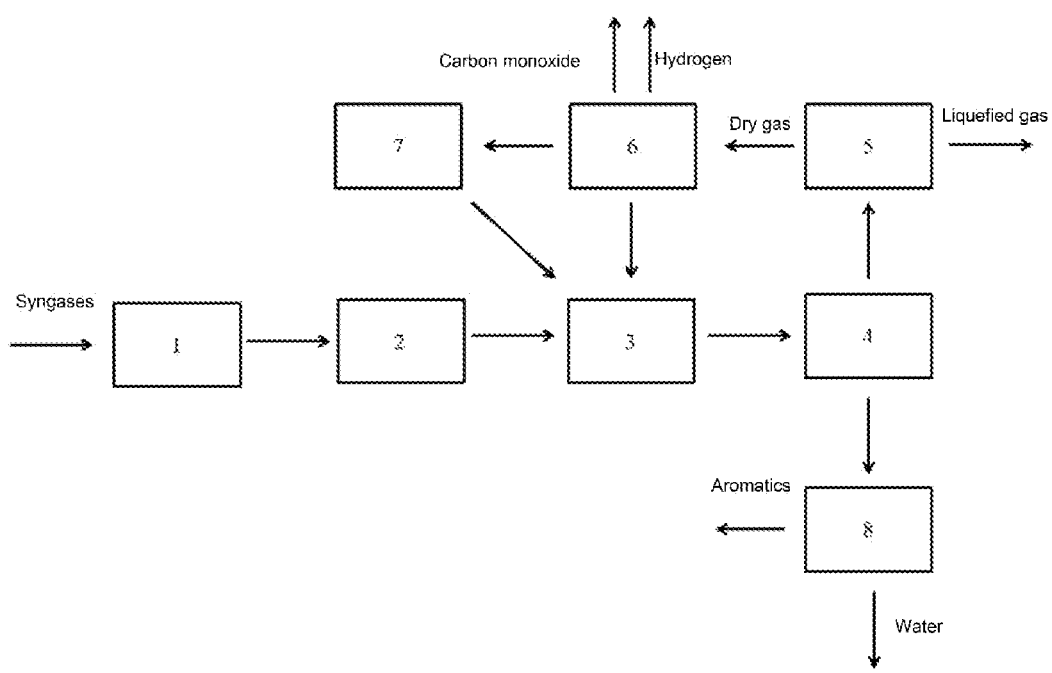
FIG. 3 is a process flow diagram of the system and process for preparing aromatics from syngases as provided in Example 6.

A system for preparing aromatics from syngases is provided in this Example, the structure of which is shown in FIG. 3. The system comprises: a syngas purification unit 1, a syngas conversion unit 2, a syngas-to-aromatics unit 3, a gas-liquid separation unit 4, a liquefied-gas separation unit 5, a dry-gas separation unit 6, a dry-gas conversion unit 7 and an oil-water separation unit 8, wherein the syngas purification unit 1, the syngas conversion unit 2, the syngas-to-aromatics unit 3, and the gas-liquid separation unit 4 are sequentially connected;

the outlets of the gas-liquid separation unit 4 are connected to the liquefied-gas separation unit 5 and the oil-water separation unit 8, respectively;

the outlets of the liquefied-gas separation unit 5 is connected to the dry-gas separation unit 6;

the outlets of the dry-gas separation unit 6 are connected to the dry-gas conversion unit 7 and the syngas-to-aromatics unit 3, respectively; and the outlet of the dry-gas conversion unit 7 is connected to the syngas-to-aromatics unit 3.

When using the system as provided in this Example to produce aromatics from syngases, a process comprising the following steps may be performed (according to the process flow diagram as shown in FIG. 3):

the syngases as raw materials are supplied into the syngas purification unit 1 for purification;

the purified syngases are introduced into the syngas conversion unit 2 to produce converted gases having a ratio of $H_2:CO=1.5:1$;

the gas is introduced into the syngas-to-aromatics unit 3 for reaction, wherein the catalyst as used comprises a support of a ZSM-5 molecular sieve, a first metal of zinc and cerium, and a second metal of iron and copper, with a ratio by mass of ZSM-5 molecular sieve, metal zinc, metal cerium, metal iron and metal copper (ZSM-5:zinc: cerium:iron:copper) of 70:3:2:12:13; the reaction is carried out at a reaction temperature of 475° C., a reaction pressure of 2.5 MPa, and a volume space velocity of 5000 $h^{-1}$; the gas is converted into a gas phase, a aqueous phase, oil-phase components such as non-aromatics, benzene, toluene, $C_8$ aromatics, $C_9$ aromatics, $C_{10}$ aromatics and heavy aromatics under the action of the catalyst, while the composition thereof is as shown in Table 6. The resultant products are introduced into the gas-liquid separation unit 4 to separate into a gas-phase product and a liquid-phase product, wherein the liquid-phase product is introduced into the oil-water separation unit 8 to separate into an oil phase and an aqueous phase, and the oil phase and aqueous phase are introduced into corresponding downstream systems for treatment, respectively.

the gas phase product separated by the gas-liquid separation unit 4 is introduced into the liquefied-gas separation unit 5 to separate into a liquefied gas and a part of ethylene and dry gas, wherein the liquefied gas and ethylene are used as products, while the dry gas is introduced into the dry-gas separation unit 6 to separate into hydrogen, carbon monoxide and methane, ethane, ethylene and carbon dioxide; among them, a part of hydrogen and a part of carbon monoxide are removed as raw materials for the subsequent processing of aromatics, and the remaining hydrogen and carbon monoxide are returned to the syngas-to-aromatics unit 3 for reaction, while methane and ethane are introduced into the dry-gas conversion unit 7 to convert into syngases, i.e. hydrogen and carbon monoxide, under a conversion temperature of 900° C. and a conversion pressure of 3.0 MPa, which products are then returned to the syngas-to-aromatics unit 3.

TABLE 6

The reaction products in the preparation of aromatics from syngases

| Products | Selectivity of hydrocarbonyls % |
|---|---|
| Dry gas | 8 |
| Liquefied gas | 18 |
| Oil-phase non-aromatics | 8 |
| Aromatics | 62 |
| CO conversion rate (excluding conversion to $CO_2$) | 27 |

What is claimed is:

1. A process for preparing aromatics from syngas by using a system comprising a syngas purification unit, a syngas conversion unit, a syngas-to-aromatics unit, a gas-liquid separation unit, a liquefied-gas separation unit, a dry-gas separation unit, a dry-gas conversion unit and an oil-water separation unit, wherein the syngas purification unit, the syngas conversion unit, the syngas-to-aromatics unit, and the gas-liquid separation unit are sequentially connected;

the gas-liquid separation unit is connected to the liquefied-gas separation unit and the oil-water separation unit, respectively;

the liquefied-gas separation unit is connected to the dry-gas separation unit;

the dry-gas separation unit is connected to the dry-gas conversion unit and the syngas-to aromatics unit, respectively; and the dry-gas conversion unit is connected to the syngas-to-aromatics unit, the process comprising:

a) supplying syngas as a raw material into the syngas purification unit for purification to obtain purified syngas;

b) introducing the purified syngas into the syngas conversion unit for conversion to obtain converted syngas;

c) introducing the converted syngas, carbon monoxide and hydrogen from the dry-gas conversion unit, carbon monoxide and hydrogen from the dry-gas separation unit into the syngas-to-aromatics unit to produce a reaction product comprising aromatics, wherein a reaction temperature in the syngas-to-aromatics unit is from 380° C. to 520° C., a volume space velocity in the syngas-to-aromatics unit is from 100 $h^{-1}$ to 100,000 $h^{-1}$, a reaction pressure in the syngas-to aromatics unit is from 1.0 MPa to 10.0 MPa, and a molar ratio of carbon monoxide to hydrogen in the converted syngas at an outlet of the syngas conversion unit is from 1.0:1 to 3.5:1;

d) cooling the reaction product comprising aromatics obtained in step c), then introducing the cooled reaction product into the gas-liquid separation unit to separate into a gas phase and a liquid phase, wherein the gas phase is introduced into the liquefied-gas separation unit to separate into a liquefied gas and a dry gas, and the liquid phase is introduced into the oil-water separation unit to separate into an oil phase and an aqueous phase;

e) introducing the dry gas obtained in step d) into the dry-gas separation unit to separate into hydrogen, carbon monoxide and methane, ethane, ethylene, and carbon dioxide; and f) introducing methane and ethane obtained in step e) into the dry-gas conversion unit to convert into syngas, that is, hydrogen and carbon monoxide, wherein a conversion pressure in the dry-gas conversion unit is 1.5 MPa to 4.0 MPa and a conversion temperature in the dry-gas conversion unit is from 800° C. to 1000° C.;

wherein in step c), a catalyst used for producing the aromatics in the syngas-to-aromatics unit is a composite catalyst which comprises a support, a first metal component, and a second metal component, wherein the support comprises one or more selected from a ZSM-5 molecular sieve, a ZSM-11 molecular sieve and a ZSM-22 molecular sieve, and is comprised in an amount of 30% to 90% of a total mass of the composite catalyst;

the first metal component is one or more selected from zinc, silver, gallium, lanthanum and cerium, and is comprised in an amount of 0.1% to 10% of the total mass of the composite catalyst;

the second metal component is one or more selected form iron, cobalt, manganese, and copper, and is comprised in an amount of 10% to 60% of the total mass of the composite catalyst, and the total mass of the support, the first metal component and the second metal component is 100% of the total mass of the composite catalyst.

2. The process according to claim 1, wherein in step d), the liquefied gas and ethylene separated by the liquefied-gas separation unit are introduced into the syngas-to-aromatics unit to produce aromatics.

3. The process according to claim 1, wherein a part of hydrogen and carbon monoxide separated by the dry-gas separation unit is introduced into an aromatics-processing unit.

4. The process according to claim 1, wherein in step f), a part of methane, ethane and ethylene obtained in step e) are removed, and all of the remaining methane and ethane obtained in step e) are introduced into the dry-gas conversion unit to convert into syngas, that is, hydrogen and carbon monoxide.

5. The process according to claim 1, wherein in step c), the volume space velocity in the syngas-to-aromatics unit is from 1,000 $h^{-1}$ to 10,000 $h^{-1}$.

6. The process according to claim 1, wherein the molar ratio of carbon monoxide to hydrogen in the converted syngas is from 1.5:1 to 3.0:1.

* * * * *